United States Patent
Rowe

[11] Patent Number: 5,827,228
[45] Date of Patent: Oct. 27, 1998

[54] SEAL MEMBERS FOR SURGICAL TROCARS

[75] Inventor: C. Daniel Rowe, Batavia, Ohio

[73] Assignee: Ethicon, Inc.

[21] Appl. No.: 569,353

[22] Filed: Feb. 16, 1996

Related U.S. Application Data

[63] Continuation of Ser. No. 46,587, Apr. 12, 1993, Pat. No. 5,545,142, which is a continuation-in-part of Ser. No. 779,040, Oct. 18, 1991, Pat. No. 5,209,736.

[51] Int. Cl.$^6$ .................................................. A61M 39/04
[52] U.S. Cl. ............................................. 604/167; 604/256
[58] Field of Search ..................................... 604/164, 167, 604/256, 169, 248, 258

[56] References Cited

U.S. PATENT DOCUMENTS

| | | |
|---|---|---|
| 1,986,484 | 1/1935 | Schueler . |
| 2,898,917 | 8/1959 | Wallace . |
| 3,313,299 | 4/1967 | Spademan ............................ 128/214.4 |
| 3,329,390 | 7/1967 | Hulsey . |
| 3,366,363 | 1/1968 | Hogan et al. . |
| 3,487,837 | 1/1970 | Petersen . |
| 3,565,078 | 2/1971 | Vailancourt . |
| 3,585,996 | 6/1971 | Reynolds et al. ..................... 128/214.4 |
| 3,620,500 | 11/1971 | Santomierl . |
| 3,703,899 | 11/1972 | Calinog . |
| 3,853,127 | 12/1974 | Spademan . |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,096,860 | 6/1978 | McLaughlin ......................... 128/214.4 |
| 4,112,932 | 9/1978 | Cirelli . |
| 4,177,814 | 12/1979 | Knepshield et al. .................... 128/348 |
| 4,180,068 | 12/1979 | Jacobsen et al. . |
| 4,187,849 | 2/1980 | Stim . |
| 4,233,982 | 11/1980 | Bauer et al. . |
| 4,240,411 | 12/1980 | Hosono . |
| 4,243,034 | 1/1981 | Brandt . |
| 4,261,357 | 4/1981 | Kontos ................................ 128/214.4 |
| 4,338,934 | 7/1982 | Spademan . |
| 4,424,833 | 1/1984 | Spector et al. . |
| 4,430,081 | 2/1984 | Timmermans . |
| 4,464,178 | 8/1984 | Dalton . |
| 4,475,548 | 10/1984 | Muto . |
| 4,512,766 | 4/1985 | Vailancourt . |
| 4,531,937 | 7/1985 | Yates . |
| 4,535,773 | 8/1985 | Yoon ........................................ 604/51 |

(List continued on next page.)

FOREIGN PATENT DOCUMENTS

| | | |
|---|---|---|
| 0 113 520 | 7/1984 | European Pat. Off. . |
| 0 206 553 | 5/1986 | European Pat. Off. . |
| 0 223 451 | 10/1986 | European Pat. Off. . |
| 0 267 584 | 11/1987 | European Pat. Off. . |
| 0 267 584 | 5/1988 | European Pat. Off. . |
| 0 316 096 | 10/1988 | European Pat. Off. . |
| 0 312 219 | 4/1989 | European Pat. Off. . |
| 0 336 903 | 4/1989 | European Pat. Off. . |
| 0 349 955 | 7/1989 | European Pat. Off. . |
| 0 350 291 | 7/1989 | European Pat. Off. . |
| 0 426 407 | 10/1990 | European Pat. Off. . |
| 0 510 851 | 4/1992 | European Pat. Off. . |
| 0 051 718 | 5/1992 | European Pat. Off. . |
| 3042229 | 8/1980 | Germany . |
| 3737 121 A1 | 11/1987 | Germany . |
| 4020956 | 6/1990 | Germany . |
| WO 93/04717 | 3/1993 | WIPO . |

Primary Examiner—Max Hindenburg
Attorney, Agent, or Firm—Rockey, Milnamow & Katz

[57] ABSTRACT

Trocar assembly devices are disclosed that include an improved elastomeric seal member to maintain sealing engagement during off-centering or radial motion of instruments extending therethrough. The seal members include an inner section and an outer section. The inner section has an opening formed therein to permit an elongate instrument to pass therethrough in sealing engagement therewith. In accordance with certain embodiments, a corrugated portion is formed in the outer section. In accordance with certain embodiments an annular floating ring separates the inner section from the outer section.

13 Claims, 8 Drawing Sheets

U.S. PATENT DOCUMENTS

| | | | |
|---|---|---|---|
| 4,540,411 | 9/1985 | Bodicky | 604/169 |
| 4,580,573 | 4/1986 | Quinn . | |
| 4,581,019 | 4/1986 | Curelaru et al. | 604/164 |
| 4,601,710 | 7/1986 | Koonz . | |
| 4,610,665 | 9/1986 | Matsumoto et al. . | |
| 4,610,710 | 9/1986 | Suzuki et al. . | |
| 4,611,785 | 9/1986 | Steer . | |
| 4,613,329 | 9/1986 | Bodicky . | |
| 4,626,245 | 12/1986 | Weinstein . | |
| 4,629,450 | 12/1986 | Suzuki et al. | 604/164 |
| 4,634,432 | 1/1987 | Kocak . | |
| 4,654,030 | 3/1987 | Moll et al. . | |
| 4,664,660 | 5/1987 | Goldberg et al. . | |
| 4,670,008 | 6/1987 | Von Albertini | 604/165 |
| 4,673,393 | 6/1987 | Suzuki et al. . | |
| 4,705,511 | 11/1987 | Kocak . | |
| 4,723,550 | 2/1988 | Bales et al. . | |
| 4,729,914 | 3/1988 | Kliment et al. | 428/36 |
| 4,758,225 | 7/1988 | Cox et al. . | |
| 4,772,264 | 9/1988 | Cragg | 604/158 |
| 4,817,631 | 4/1989 | Schnepp-Pesch et al. . | |
| 4,842,591 | 6/1989 | Luther . | |
| 4,857,062 | 8/1989 | Russell . | |
| 4,862,891 | 9/1989 | Smith | 128/343 |
| 4,869,717 | 9/1989 | Adair . | |
| 4,874,378 | 10/1989 | Hillstead . | |
| 4,909,798 | 3/1990 | Fleischhacker et al. . | |
| 4,917,668 | 4/1990 | Haindl . | |
| 4,929,235 | 5/1990 | Merry et all . | |
| 4,932,623 | 6/1990 | Johnson et al. . | |
| 4,935,008 | 6/1990 | Lewis, Jr. | 604/42 |
| 4,938,259 | 7/1990 | Schmidt . | |
| 4,943,280 | 7/1990 | Lander . | |
| 4,950,257 | 8/1990 | Hibbs et al. | 604/265 |
| 4,954,130 | 9/1990 | Edwards | 604/169 |
| 4,960,412 | 10/1990 | Fink . | |
| 4,966,588 | 10/1990 | Rayman et al. . | |
| 4,978,334 | 12/1990 | Toye et al. | 604/51 |
| 4,978,341 | 12/1990 | Niederhauser . | |
| 4,981,482 | 1/1991 | Ichikawa | 606/108 |
| 4,994,027 | 2/1991 | Farrell | 604/53 |
| 5,000,745 | 3/1991 | Guest et al. . | |
| 5,002,557 | 3/1991 | Hasson . | |
| 5,009,643 | 4/1991 | Reich et al. | 604/165 |
| 5,030,206 | 7/1991 | Lander | 604/164 |
| 5,041,095 | 8/1991 | Littrell . | |
| 5,041,097 | 8/1991 | Johnson | 604/167 |
| 5,059,186 | 10/1991 | Yammamoto et al. . | |
| 5,073,169 | 12/1991 | Raiken et al. . | |
| 5,092,846 | 3/1992 | Nishijima et al. | 604/165 |
| 5,103,854 | 4/1992 | Bailey et al. . | |
| 5,104,383 | 4/1992 | Shichman . | |
| 5,108,380 | 4/1992 | Herlitze et al. . | |
| 5,112,308 | 5/1992 | Olsen et al. | 604/164 |
| 5,127,626 | 7/1992 | Hilal et al. . | |
| 5,137,520 | 8/1992 | Maxson et al. . | |
| 5,158,553 | 10/1992 | Berry et al. . | |
| 5,167,636 | 12/1992 | Clement . | |
| 5,180,373 | 1/1993 | Green et al. | 604/167 |
| 5,197,955 | 3/1993 | Stephens et al. | 604/167 |
| 5,207,714 | 5/1993 | Gentelia et al. . | |
| 5,209,736 | 5/1993 | Stephens et al. . | |
| 5,209,737 | 5/1993 | Ritchart et al. | 604/167 |
| 5,211,370 | 5/1993 | Powers | 251/4 |
| 5,221,264 | 6/1993 | Wilk et al. . | |
| 5,226,891 | 7/1993 | Bushatz et al. . | |
| 5,242,412 | 9/1993 | Blake, III . | |
| 5,312,363 | 5/1994 | Ryan et al. . | |
| 5,334,164 | 8/1994 | Guy et al. . | |
| 5,342,315 | 8/1994 | Rowe et al. . | |
| 5,350,364 | 9/1994 | Stephens et al. | 604/256 X |
| 5,366,446 | 11/1994 | Tal et al. . | |
| 5,380,288 | 1/1995 | Hart et al. . | |
| 5,385,553 | 1/1995 | Hart et al. | 604/256 X |
| 5,391,154 | 2/1995 | Young . | |
| 5,395,342 | 3/1995 | Yoon . | |
| 5,411,483 | 5/1995 | Loomas et al. . | |
| 5,531,758 | 7/1996 | Uschold et al. | 604/167 X |
| 5,545,142 | 8/1996 | Stephens et al. | 604/167 |

SEAL MEMBERS FOR SURGICAL TROCARS

This application is a continuation of application Ser. No. 08/046,587, filed Apr. 17, 1993, now U.S. Pat. No. 5,454,142 which is a continuation in part of application Ser. No. 07/779,040 filed Oct. 18, 1991, now U.S. Pat. No. 5,209,736.

FIELD OF THE INVENTION

This invention generally relates to surgical instruments; and more particularly, the invention relates to surgical trocar assembly devices for providing communication into an anatomical cavity. The trocar assembly devices in accordance with the present invention include an improved seal member that is able to maintain sealing engagement during off-centering or radial motion of elongate surgical instruments extending therethrough.

BACKGROUND OF THE INVENTION

A trocar assembly is a surgical instrument that is used to gain access to a body cavity. A trocar assembly generally comprises two major components, a trocar tube and an obturator. The trocar tube having the obturator inserted therethrough is directed through the skin to access a body cavity through the tube in which laparoscopic or arthroscopic surgery and endoscopic procedures are to be performed. In order to penetrate the skin, the distal end of the trocar tube is placed against the skin which has been cut with a scalpel. The obturator has a sharp point or cutting edge at its distal end. By applying pressure against the proximal end of the obturator, the sharp point is forced through the skin until it enters the body cavity. The trocar tube is inserted through the perforation made by the obturator and the obturator is withdrawn, leaving the trocar tube as an accessway to the body cavity. Examples of trocar assembly devices are disclosed in U.S. Pat. No. 4,535,773.

The proximal end portion of the trocar tube is typically adjoined by a housing that defines a chamber having an open distal end portion that communicates with the interior lumen defined by the trocar tube. An obturator and other elongate surgical instruments or tools axially extend into and are withdrawn from the trocar tube through the proximal end portion of the chamber. It is the present practice to provide the chamber with a sealing means, such as a sealing grommet or gasket, through which the obturator or other instruments extend. The sealing means seals against the outer surface of the inserted instruments and thereby prevents fluids and insufflation gas from leaving or entering the body cavity through the trocar tube.

It is typically necessary to manipulate a surgical instrument extending through the trocar assembly during a surgical procedure. In so doing, the off-centering or non-axial orientation of the instrument as it extends through the sealing means may prevent the sealing means from maintaining sealing engagement with the instrument. Accordingly, there is a need for a trocar assembly that includes a sealing means that maintains sealing engagement with an instrument extending therethrough during off-centering of the instrument. It is also desirable for the sealing means to include means to guide an instrument extending therethrough in a manner that minimizes insertion and drag forces as the instrument is inserted and withdrawn from the trocar assembly.

SUMMARY OF THE INVENTION

In accordance with the principles of the present invention, trocar assembly devices are provided that include an improved seal member or gasket that accommodates and maintains sealing engagement with off-centered instruments extending therethrough. The seal member is generally a bellows-type or corrugated seal that is made from an elastomeric material. The seal member includes an opening formed through an inner section thereof that is dimensioned to accommodate instruments extending therethrough in a particular preselected size range. A corrugated portion is formed in an outer section of the seal member in surrounding relationship with the opening so as to enhance flexibility of the outer section of the seal member and thereby maintain the sealing engagement of the inner section of the seal with an elongate instrument extending therethrough in an off-centered orientation.

In accordance with a preferred embodiment of the invention, the exterior section of the seal member has a peripheral flange portion that is secured to the housing of the trocar assembly. In accordance with another preferred embodiment of the invention, the outer section includes a peripheral wall portion having an annular groove formed therein that receives a cooperating tongue portion, associated with the housing, in sealing engagement therewith.

The seal means in accordance with the invention further contemplates the inclusion of guide means to facilitate the insertion and withdrawal of elongate instruments from the trocar assembly. The guide means includes a plurality of spaced apart projections or ribs that extend outwardly from the outer surface of the inner section of the seal member to reduce surface contact between the instrument and the seal member as it is inserted through the opening. In accordance with a preferred embodiment of the invention, the projections are a plurality of spaced apart radially extending ribs that are formed integrally with the inner section. The ribs preferably extend from at least a portion of the corrugated portion of the seal member. In accordance with another preferred embodiment of the invention, radial ribs also extend from an inner surface of the inner section of the seal member to reduce surface contact with an elongate instrument as it is being withdrawn through the opening of the seal member. The ribs formed in the inner surface are preferably not in axial alignment with the ribs formed in the outer surface. The inner end portion of the ribs are spaced a short distance from the opening of the seal member.

In accordance with another aspect of the invention, an elastomeric seal member is provided that includes an inner section and an outer section. The inner section includes an opening formed therein for permitting an elongate instrument to pass therethrough in sealing engagement therewith. An annular floating ring is provided to separate and isolate the inner and outer sections so that off-center movement of an instrument extending through the opening causes lateral movement of the outer section while maintaining the inner section in sealing engagement with the instrument.

The floating ring may be formed from a rigid or semi-rigid material. The ring may be integrally formed with the seal member as an annular area of increased thickness. Alternatively, the ring may comprise an annular plastic member molded into and separating the inner and outer sections of the seal member. In accordance with a further alternative embodiment of the invention, the ring may comprise a first substantially rigid annular member secured to one of the surfaces of the seal member. A second rigid annular member may be secured to the other surface of the seal member. These members may also be secured to each other.

BRIEF DESCRIPTION OF THE DRAWINGS

A more complete appreciation of this invention, and many of the attendant advantages thereof will be readily apparent as the same becomes better understood by reference to the following detailed description, when considered in conjunction with the accompanying drawings, in which like reference numerals indicate the same or similar components, wherein:

FIG. 1 is a cross-sectional view taken through a trocar assembly device that includes a seal member constructed in accordance with a preferred embodiment of the invention;

FIG. 2 is a cross-sectional view of the trocar assembly shown in FIG. 1 through a plane that is oriented 90° from the plane through which FIG. 1 is taken;

FIG. 3 is a cross-sectional view taken along line 3—3 in FIG. 2;

DETAILED DESCRIPTION OF PREFERRED EMBODIMENTS

Figures 1, 2, 3:
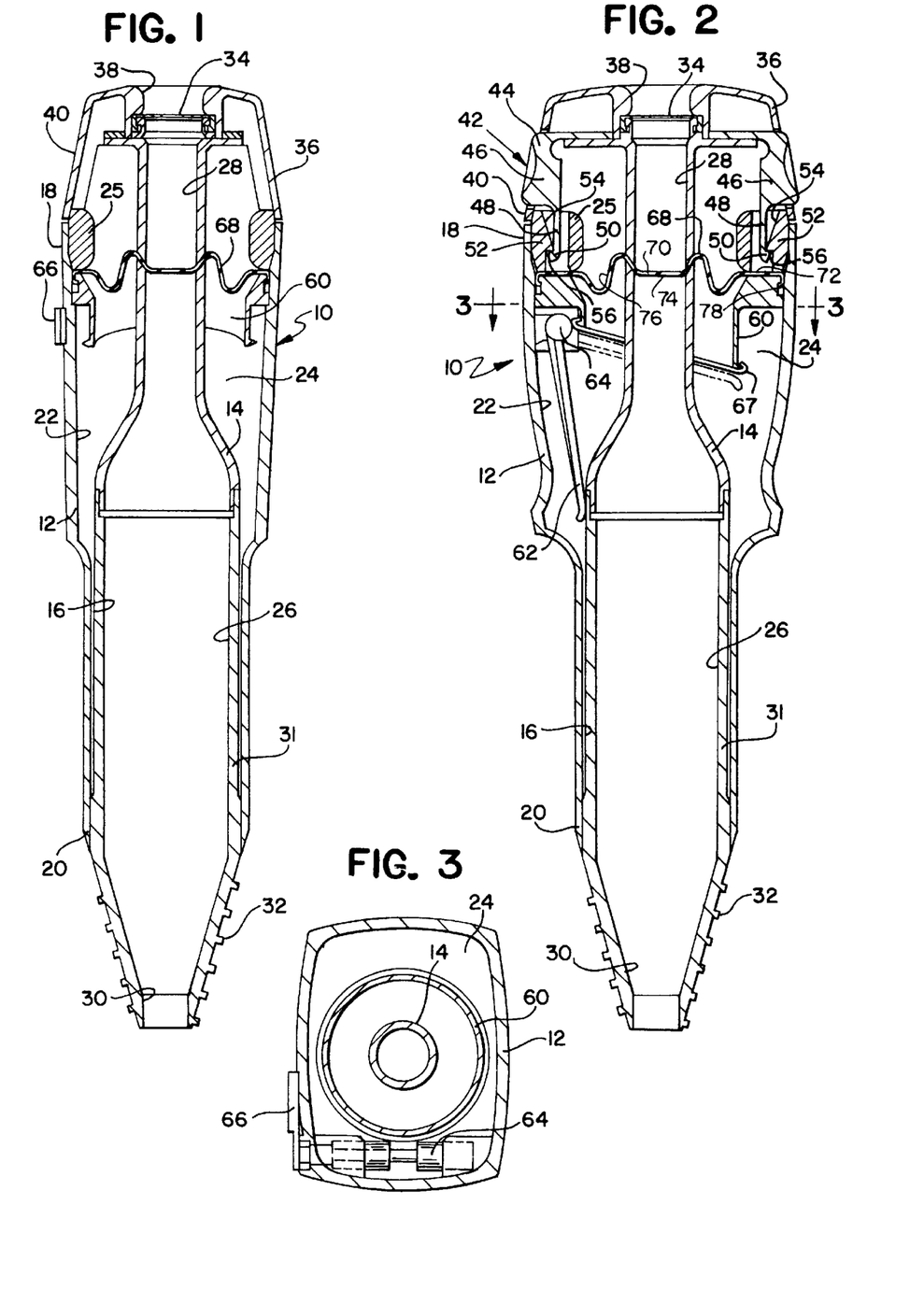

Referring to FIGS. 1–3, an exemplary trocar assembly 10 is shown that includes a seal member constructed in accordance with the invention as disclosed in copending U.S. patent application Ser. No. 07/779,040, which disclosure is incorporated herein by reference. The particular construction of the trocar assembly does not form a part of the invention. Trocar assembly 10 includes an outer trocar tube 12 and an inner trocar tube 14. Inner trocar tube 14 is extendable through outer trocar tube 12.

Outer trocar tube 12 defines an interior lumen 16 and has an open proximal end portion 18 and an open distal end portion 20. The inner diameter of trocar tube 12 at its distal end of distal end portion 20 is preferably in the range from about 15.0 mm to about 50.0 mm, and most preferably in the range from about 30.0 mm to about 40.0 mm. The proximal end portion 18 of outer trocar tube 12 is of increased dimensions to form a handle or housing portion 22 defining a chamber 24. The opening in the proximal end of the housing is defined by ring portion 25.

Inner trocar tube 14 defines an interior lumen 26 and has an open proximal end portion 28 and an open distal end portion 30. The inner diameter of trocar tube 14 at the distal end of its distal end portion 30 is preferably in the range from about 5.0 mm to about 15.0 mm, and most preferably in the range from about 10.0 mm to about 12.0 mm. For reasons that will hereinbelow become more apparent, trocar tube 14 has an intermediate portion 31 that has an increased diameter such that the outer surface thereof slidingly contacts the inner surface of outer trocar tube 12. The inner diameter of the proximal end portion 28 of trocar tube 14 is substantially equal to the inner diameter of distal end portion 30. The distal end portion 30 extends distally beyond the distal end of trocar tube 12 and tapers inwardly as it extends towards the distal end thereof. The outer surface of distal end portion 30 preferably has square toothed helical threads 32 formed thereon.

The proximal end portion 28 of inner trocar tube 14 is provided with an annular or apertured sealing gasket 34 to seal against an implement directed therethrough, as is well known in the art. A cap member 36 is attached to the proximal end portion 28 and has an opening 38 in axial alignment with the opening in sealing gasket 34. Cap member 36 has side walls 40 that extend towards the proximal edge of housing portion 22.

As best seen in FIG. 2, a latch assembly 42 is provided to releasably attach cap member 36 and inner trocar tube 14 attached thereto to housing portion 22 of outer trocar tube 12 via ring 25 attached to housing portion 22. Latch assembly 42 includes a latch member 44 having a pair of flexible latch activator portions 46 that extend outwardly from openings through opposite sides of cap member 36 and a latch finger portion 48 defining a retaining flange portion 50 associated with each activator portion 46. Ring 25 of the outer trocar is formed with a pair of retaining portions 52 each of which defines a ramp section 54 and a recessed or lip section 56. As inner trocar tube 14 is extended into outer trocar tube 12 the flange portions 50 of finger portions 48 of latch member 44 contact a corresponding ramp section 54 and are deflected inwardly as they ride down ramp section 54. When the flange portions 50 reach the lip sections 56 they snap outwardly into locking engagement therewith, as shown in FIG. 2. When it is necessary to remove trocar tube 14 from trocar tube 12, the activator portions 46 are depressed inwardly causing the flange portions 50 to move inwardly beyond the inner projections of lip sections 56, thus permitting trocar tube 14 to be removed from trocar tube 12.

A generally tubular valve seat member 60 is located in chamber 24 at the proximal end portion 18 of outer trocar tube 12. The distal end of valve seat member 60 is preferably angled, as best seen in FIG. 2. A flap valve member 62 of known construction is suitably hinged at 64 and is movable between a sealing position in sealing engagement with valve seat member 60, as shown in phantom lines in FIG. 2, and an open position removed from valve seat member 60, as shown in solid lines in FIG. 2. Valve member 62 is biased into its sealing position by a suitable spring means (not shown). A lever member 66 located outside of chamber 24 is attached to hinge 64 to permit manual movement of valve member 62 between its sealing position against a sealing gasket 67 attached to seat 60 into its open position against the spring bias. A sealing gasket 68 is provided at the proximal end of valve seat member 60 to seal against the outer surface of trocar tube 14 or an implement as it extends therethrough. Sealing gasket 68 is a bellows-type seal constructed in accordance with the invention to facilitate maintaining a seal during radial motion of instruments inserted therethrough.

Sealing gasket 68 includes a generally planar inner section 70 and an outer section 72. An opening 74 is formed through inner section 70 for allowing an elongate instrument to pass therethrough in sealing engagement therewith. A corrugated portion 76 is formed in outer section 72 in surrounding relationship with opening 74 so as to maintain the sealing engagement with an elongate implement during off-centering or radial motion of the implement with respect to the seal member. The corrugated portion 76 extends above and below a plane extending through the inner section 70. The outer section 72 has a peripheral flange portion 78 that is suitably mounted in sealing engagement with outer trocar tube 12. The corrugated portion 76 increases the flexibility of the outer section 72 of seal member 68 to enhance the sealing engagement of the seal member.

Referring to FIGS. 4–9, there is shown an alternative trocar assembly device 100 incorporating a seal member 134 constructed in accordance with the invention. The particular construction of the trocar assembly device 100 does not form a part of the invention.

Figures 4, 5:
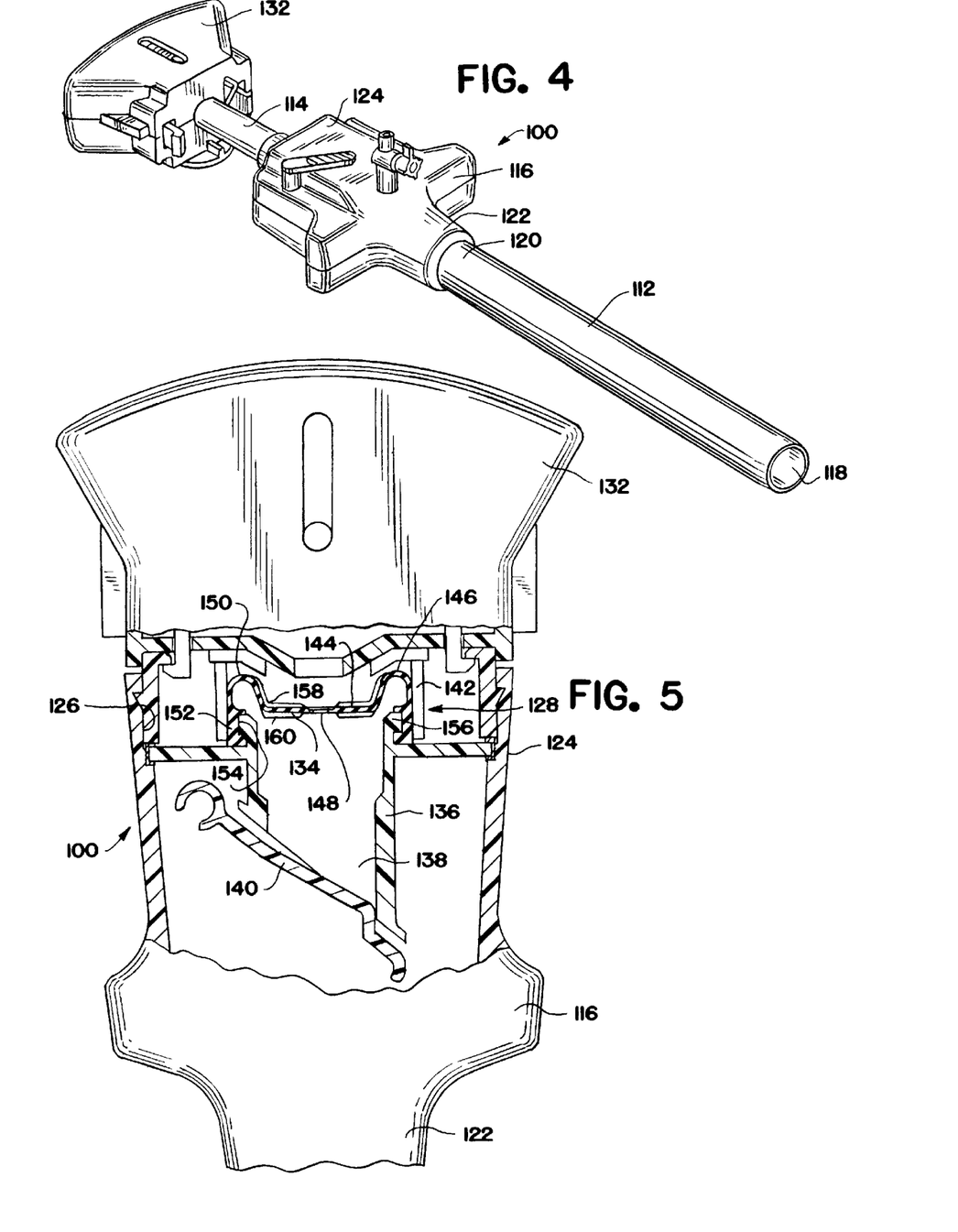
FIG. 4 is a perspective view of another embodiment of a trocar assembly device of the type that includes a seal member constructed in accordance with the invention, with an obturator partially extended into the trocar tube.
FIG. 5 is an elevational view, partially in cross-section, of the trocar assembly device shown in FIG. 4, with the obturator handle attached to the trocar tube and the obturator removed, showing an alternative embodiment of a seal member assembly constructed in accordance with the invention.

Trocar assembly device 100 includes a trocar tube 112, an obturator 114, and a housing or handle 116. Trocar tube 112 defines an interior lumen having an open distal end portion 118 and an open proximal end portion 120. Proximal end portion 120 extends into and is mounted in a distal end portion 122 of handle 116. Handle 116 has an open proximal end portion 124 that defines an opening 126. Opening 126 is provided with a seal member assembly 128 that includes a seal member 134 constructed in accordance with the present invention and described in detail herein-below.

Obturator 114 is slidably and removably extendable within trocar tube 112 and is inserted into handle 116 and trocar tube 112 through seal member assembly 128 and opening 126. An obturator handle 132 is provided at the proximal end of the obturator and a sharpened point or blade (not shown) is formed at the distal end thereof. As is well known in the art, seal member assembly 128 cooperates with obturator 114, or a surgical instrument extending through trocar tube 112, to sealingly engage the outer surface thereof and thereby preclude the passage of fluids through handle 116.

Figure 6:
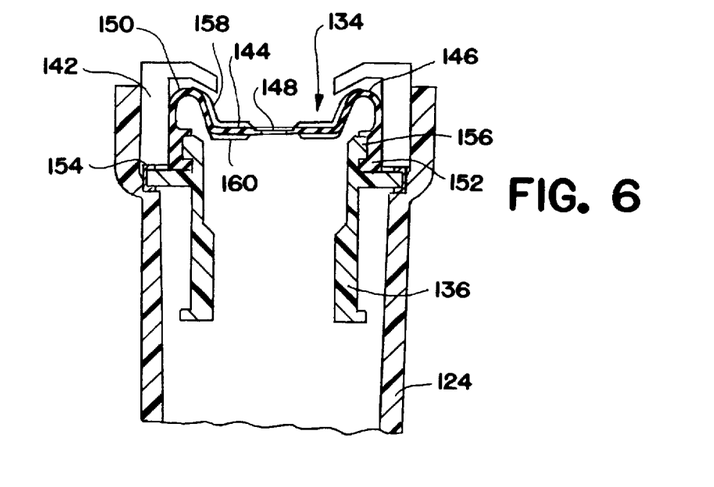
FIG 6 is a cross-sectional view of a portion of the trocar assembly shown in FIG. 5 through a plane that is oriented 90° from the plane through which the cross-section of FIG. 5 is taken.

A flap valve assembly 136 is suitably supported in end portion 124. Flap valve assembly 136 defines a passageway 138 having a hinged flap valve 140 at the distal end thereof and an elastomeric seal member 134 at the proximal end thereof. A rigid or flexible guide/retainer 142 is preferably secured within end portion 124 to guide an obturator or implement through seal member 134 into passageway 138 and to retain the seal member.

Referring to FIGS. 5–9, the elastomeric seal member 134, constructed in accordance with the invention, includes a generally planar inner section 144 and an outer section 146. An opening 148 is formed through inner section 144 and is dimensioned to permit an obturator or implement to pass therethrough in sealing engagement therewith. A corrugated portion 150 is formed in outer section 146 in surrounding relationship with opening 148. Corrugated portion 150 extends proximally from a plane passing through inner section 144. The inner section 144 may be formed with a greater thickness than corrugated portion 150. Outer section 146 is formed with a distally extending peripheral wall or flange portion 152 having an inwardly facing annular groove or recess 154 formed therein. Flange portion 152 is generally in axial alignment with corrugated portion 150. A tongue portion 156 associated with the flap valve assembly 136 is received in sealed relationship with groove 154.

Figures 7, 8, 9:
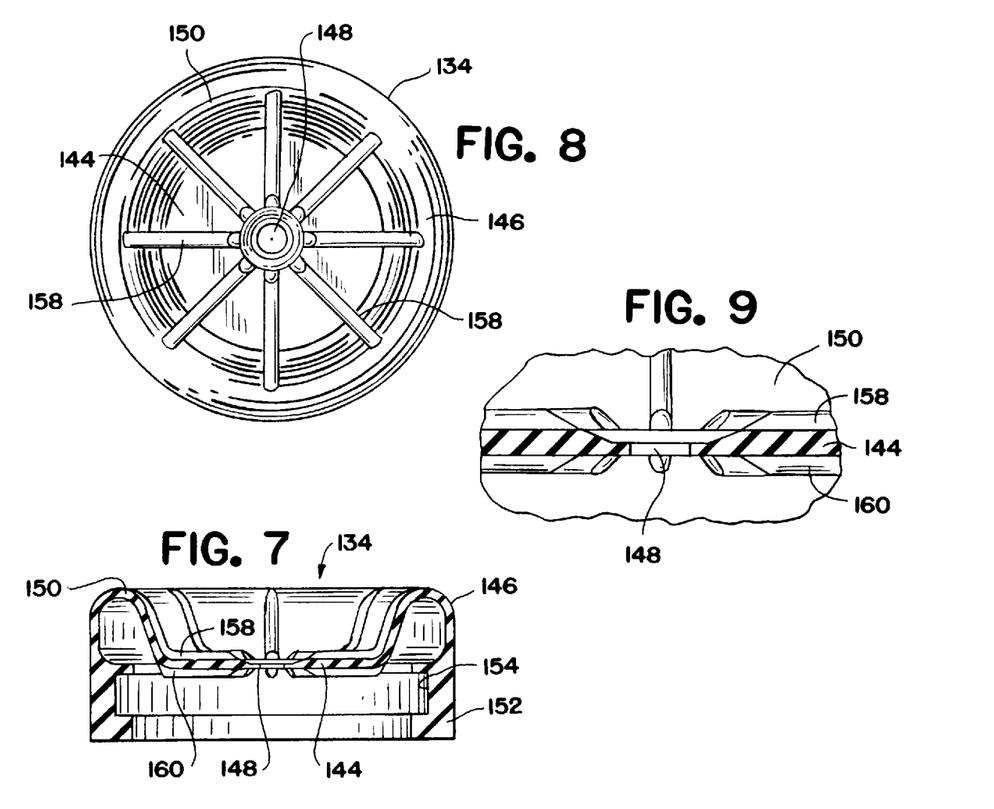
FIG. 7 is an enlarged cross-sectional view of the seal member shown in FIGS. 5–6.
FIG. 8 is a top plan view of the seal member shown in FIG. 7.
FIG. 9 is an enlarged cross-sectional view of the center portion of the seal member shown in FIG. 7.

In accordance with an alternative embodiment of the invention, a plurality of spaced apart projections or ribs 158 may be provided to extend outwardly from the proximally facing surface of the seal member and radially with respect to opening 148. Projections 158 may be integrally formed in inner section 144 and a portion of corrugated portion 150. In accordance with another embodiment of the invention, a plurality of similar radially extending ribs 160 extend outwardly from the distally facing surface of the seal member and radially with respect to the opening 148. Ribs 160 are preferably not in axial alignment with ribs 158 and only extend from the inner section 144. Referring to FIG. 9, the ribs 158 and 160 have inner end portions that are spaced a short distance from opening 148 and beveled outwardly and away from the inner portion 144 of seal member 134 to guide an instrument through opening 148. The ribs 158 and 160 are oriented to form about a 45 degree angle with an immediately adjacent rib.

In operation, as an elongate obturator or instrument is directed through opening 148 in seal member 134 in an off-centered relationship thereto, the corrugated portion 150 enhances the flexibility of the outer section 146 of seal member 134 to maintain sealing engagement between the inner section 144 of the seal member and the implement.

The projections or ribs 158 serve to reduce surface contact between the outer surface of the seal member and the instrument and thereby facilitate the insertion of the instrument through opening 148 into housing 116. The projections or ribs 160 serve to reduce surface contact between the inner surface of the seal member and the instrument and thereby facilitate the removal of the instrument from the housing 116 through opening 148.

Figure 10:
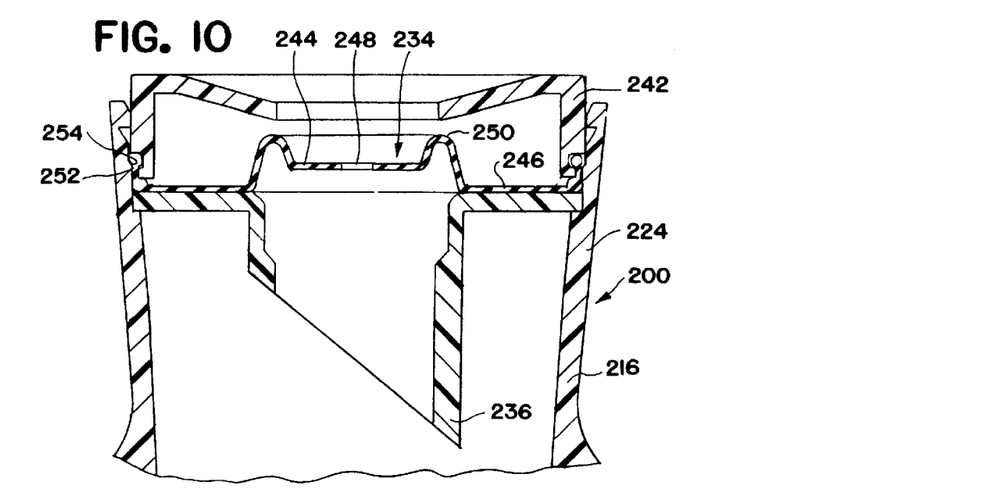
FIG. 10 is a cross-sectional view of an alternative embodiment of a seal member assembly that includes a seal member constructed in accordance with an alternative embodiment of the invention.

Referring to FIGS. 10–13, there is shown another embodiment of a seal member 234 constructed in accordance with the present invention. Seal member 234 is shown positioned in an exemplary trocar assembly 200 having a housing 216. Housing 216 has a proximal end portion 224 that is provided with a flap valve assembly 236, a portion of which is shown in FIG. 10.

Seal member 234 includes a circular inner section 244 and a generally oval outer section 246. An opening 248 is formed through inner section 244 to permit an obturator or implement to pass therethrough in sealing engagement therewith. A corrugated portion 250 is formed in outer section 246 in surrounding relationship with opening 248. Corrugated portion 250 extends proximally of a plane passing through inner section 244. Outer section 246 is formed with a proximally extending peripheral wall or lip 252 that is generally perpendicular to inner section 246. The outer edge of wall 252 is formed as a bead portion 254 that is received in sealing engagement between a guide/retainer 242 and the inner surface of end portion 224.

Figures 11, 12, 13:
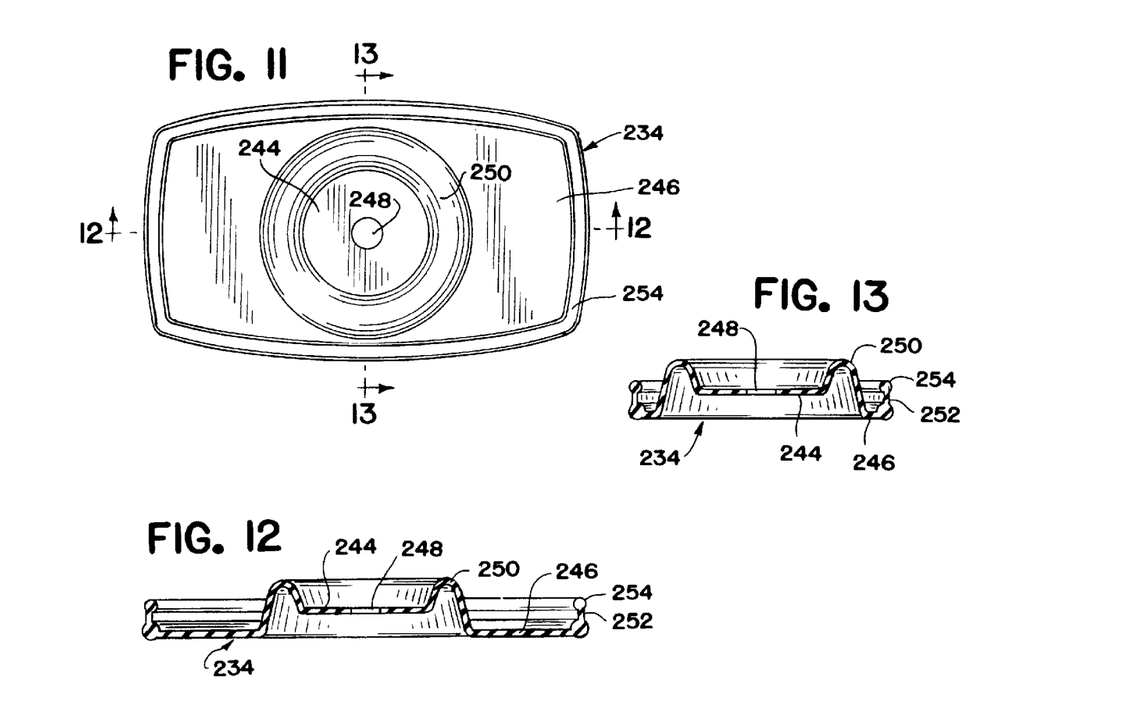
FIG. 11 is a top plan view of the seal member shown in FIG. 10.
FIG. 12 is a cross-sectional view taken along line 12—12 in FIG. 11.
FIG. 13 is a cross-sectional view taken along line 13—13 in FIG. 11.

The seal member 234 may be provided with radially extending ribs or projections (not shown) similar to ribs 158 or 160 discussed above with respect to seal member 134. The operation of seal member 234 is similar to that discussed above with respect to seal member 134.

Figure 14:
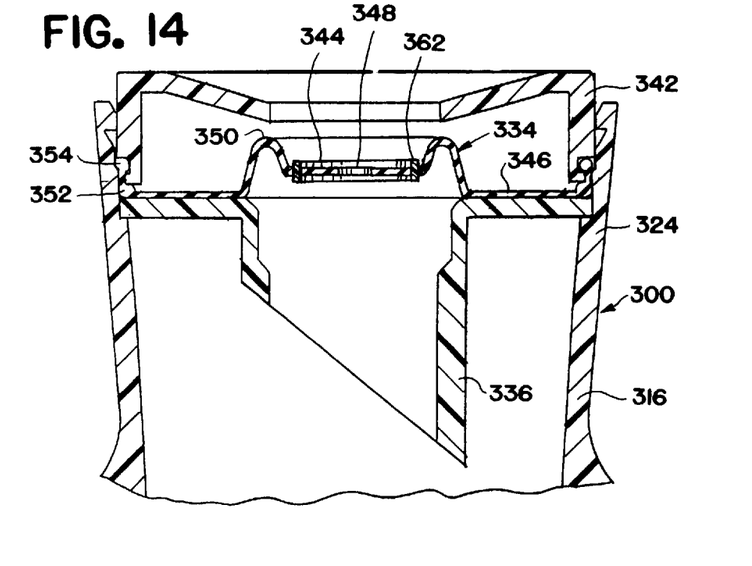
FIG. 14 is a cross-sectional view of an alternative embodiment of a seal member assembly that includes a seal member constructed in accordance with an alternative embodiment of the invention.

Referring to FIGS. 14–17, there is shown another embodiment of a seal member 334 constructed in accordance with the present invention. Seal member 334 is similar in construction to seal member 234 with the addition of an annular floating ring that separates and isolates the inner section from the outer section to facilitate movement of the outer section while maintaining the inner section in sealing engagement with an instrument. Seal member 334 is shown positioned in an exemplary trocar assembly 300 having a housing 316. Housing 316 has a proximal end portion 324 that is provided with a flap valve assembly 336, a portion of which is shown in FIG. 14.

Seal member 334 includes a circular inner section 344 and a generally oval outer section 346. An opening 348 is formed through inner section 344 to permit an obturator or instrument to pass therethrough in sealing engagement therewith. A corrugated portion 350 is formed in outer section 346 in surrounding relationship with opening 348. Corrugated portion 350 extends proximally from a plane passing through inner section 344. Outer section 346 is formed with a proximally extending peripheral wall or lip 352 that is generally perpendicular to inner section 346. The proximal edge of wall 352 is formed as a bead position 354 that is received in sealing engagement between a guide/retainer 342 and the inner surface of end portion 324.

Figures 15, 17:
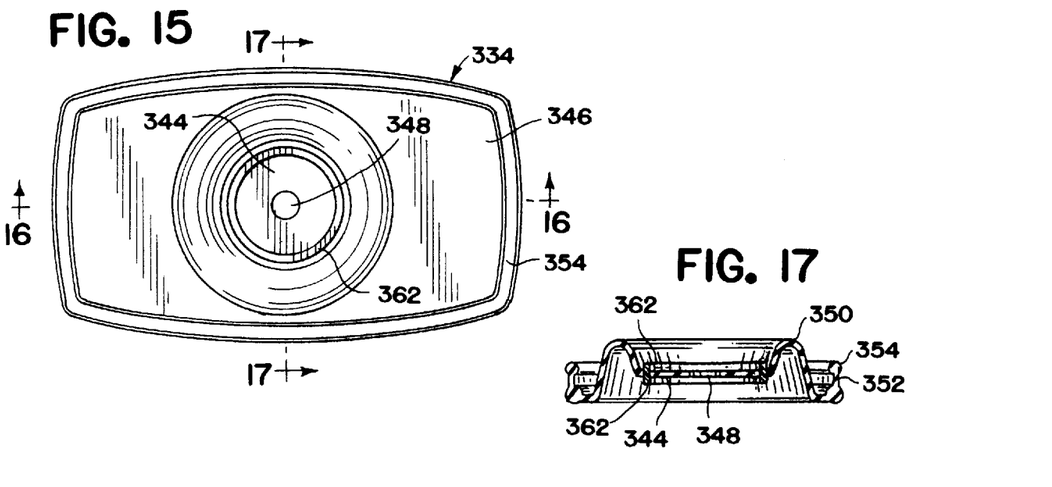
FIG. 15 is a top plan view of the seal member shown in FIG. 14.
FIG. 17 is a cross-sectional view taken along line 17—17 in FIG. 15.
Figure 16:
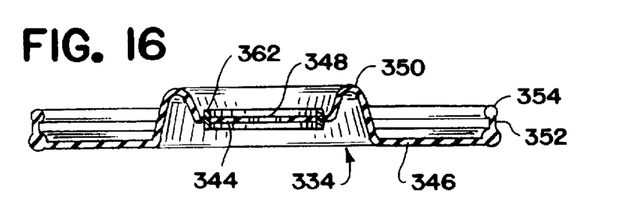
FIG. 16 is a cross-sectional view taken along line 16—16 in FIG. 15.

The inner section 344 may be provided with radially extending ribs or projections (not shown) similar to ribs 158 or 160 discussed above with respect to seal member 134.

An annular floating ring portion 362 separates inner section 344 from outer section 346. Floating ring portion 362 extends outwardly from either the proximally and/or the distally facing surfaces of seal member 334. Floating ring portion 362 is preferably molded integrally with the seal member so as to form a semi-rigid ring or collar. Alternatively, floating ring portion 362 may be formed of a rigid or semi-rigid material, such as plastic, metal or the like, that is either molded into the seal member or suitably attached thereto.

The operation of seal member 334 is similar to that discussed above with respect to seal member 134. The floating ring portion 362 allows the inner section 344 to seal against an instrument and the outer section 346 to be compliant and move laterally with off-center (or sideways) forces on the instrument. In so doing, the inner section 344 is isolated and the sideways movement of the instrument does not disrupt the seal, but instead deflects the outer section 346 that is external to the ring portion 362.

Figure 18:
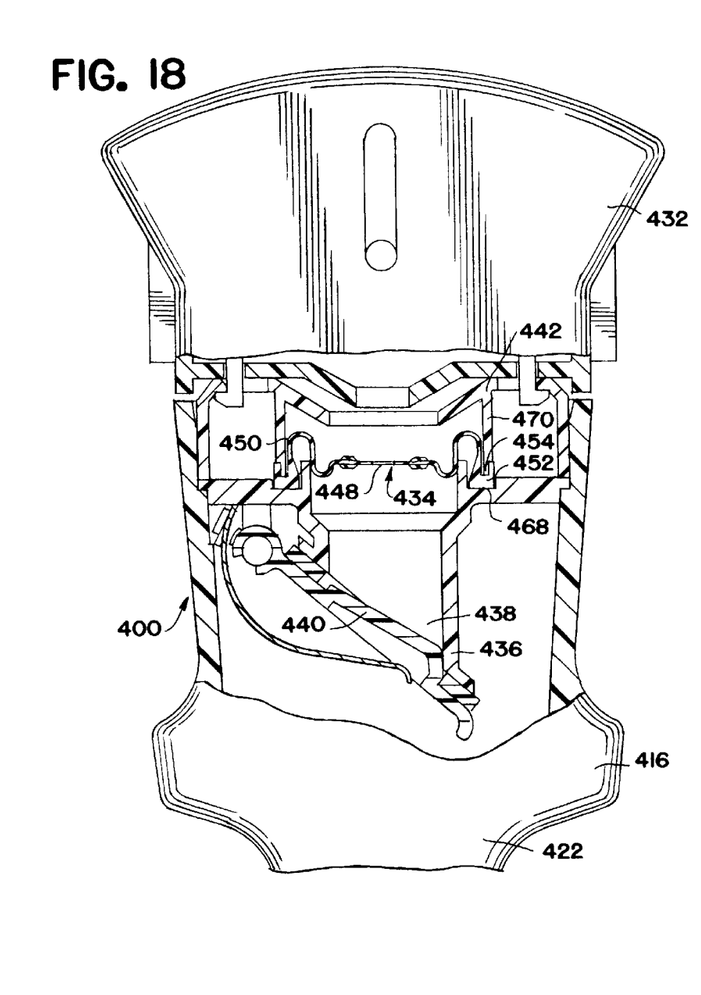
FIG. 18 is an elevational view, partially in cross-section, of an alternative embodiment of a trocar assembly device, with the obturator removed, showing an alternative embodiment of a seal member assembly constructed in accordance with the invention.
Figure 19:
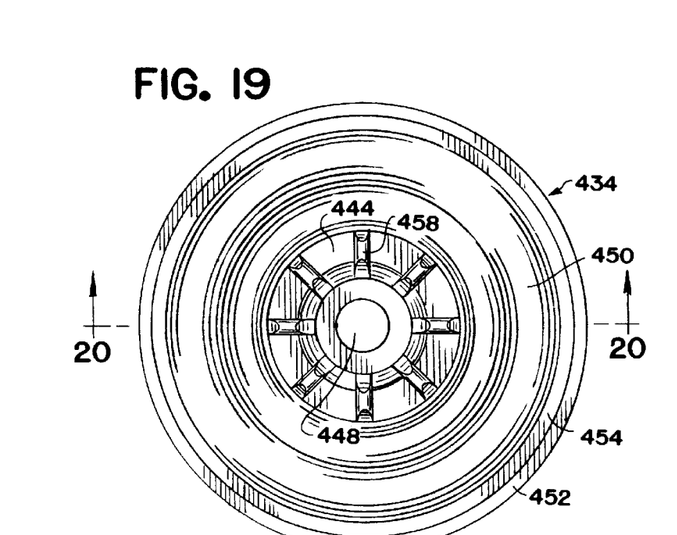
FIG. 19 is a top plan view of the seal member shown in FIG. 18.
Figure 20:
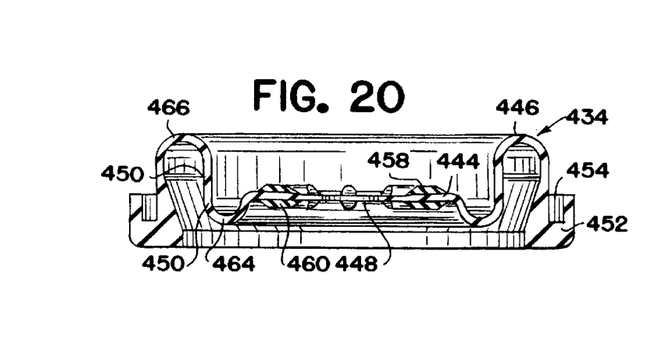
FIG. 20 is a cross-sectional view taken along line 20—20 in FIG 19.

Referring to FIGS. 18–20, there is shown yet another embodiment of a seal member 434 constructed in accordance with the present invention wherein the corrugated portion 450 includes at least two corrugations formed therein. Seal member 434 is shown positioned in an exemplary trocar assembly 400 having a housing 416. Housing 416 has a proximal end portion 424 that is provided with a flap valve assembly 436.

Seal member 434 includes a circular inner section 444 and a generally circular outer section 446. An opening 448 is formed through inner section 446 to permit an obturator or implement to pass therethrough in sealing engagement therewith. A corrugated portion 450 is formed in outer section 446 in surrounding relationship with opening 448. Corrugated portion 450 includes an inner corrugation 464 and an outer corrugation 466. Inner corrugation 464 extends distally of the plane that passes through inner section 444 and outer corrugation 466 extends proximally of such plane. Outer section 446 is formed with a proximally extending annular flange portion 452 having a groove or recess 454 formed therein. Flange portion 452 is received in an annular recess 468 formed in flap valve assembly 436. A rigid or flexible guide/retainer member 442 is provided to guide an obturator or implement through seal member 434 into passageway 438. Guide/retainer member 442 includes a distally extending flange portion 470 that is received in recess 454 to retain seal member 434 in sealing engagement with flap valve assembly 436.

A plurality of spaced apart projections or ribs 458 may be provided to extend outwardly from the proximally facing surface of the seal member and radially with respect to opening 448. Projections 458 are integrally formed in inner section 144. A plurality of similar radially extending ribs 460 may be provided to extend outwardly from the distally facing surface of the seal member. Ribs 460 may, or may not, be in axial alignment with ribs 458. The inner and outer end portions of ribs 458 and 460 are beveled as shown in FIG. 20.

The operation of seal member 434 is similar to that discussed above with respect to seal member 134.

Figure 21:
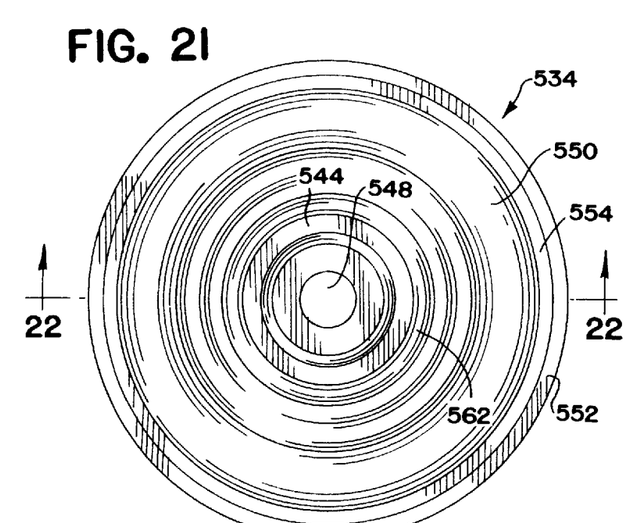
FIG. 21 is a top plan view of another alternative embodiment of a seal member construction in accordance with the invention.
Figure 22:
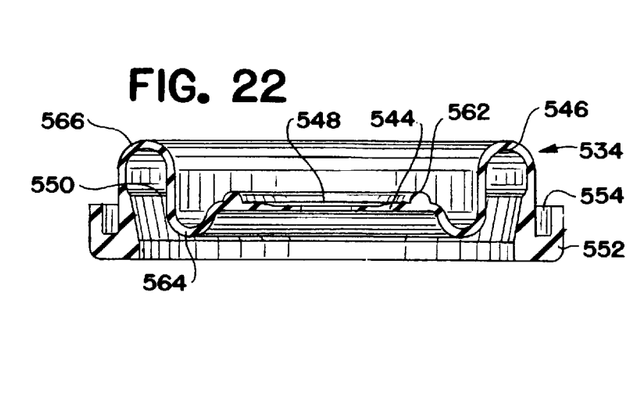
FIG. 22 is a cross-sectional view taken along line 22—22 in FIG. 21.

Referring to FIGS. 21–22, there is shown a further embodiment of a seal member 534 constructed in accordance with the invention. Seal member 534 is similar in construction to seal member 434 and includes a floating annular ring portion 562 that separates the inner section 544 and the outer section 546. The common elements of seal members 434 and 534 are identified by reference numerals having the same last two digits and reference is made to the above discussion of such elements.

Floating ring portion 562 is shown extending proximally from the outer surface of seal member 534 and is molded integrally therewith. However, the floating ring portion 362 may be alternatively formed as discussed above with respect to seal member 334. As shown in FIG. 22, the outer portion of inner section 544 may be formed to have an increased thickness.

Figure 23:
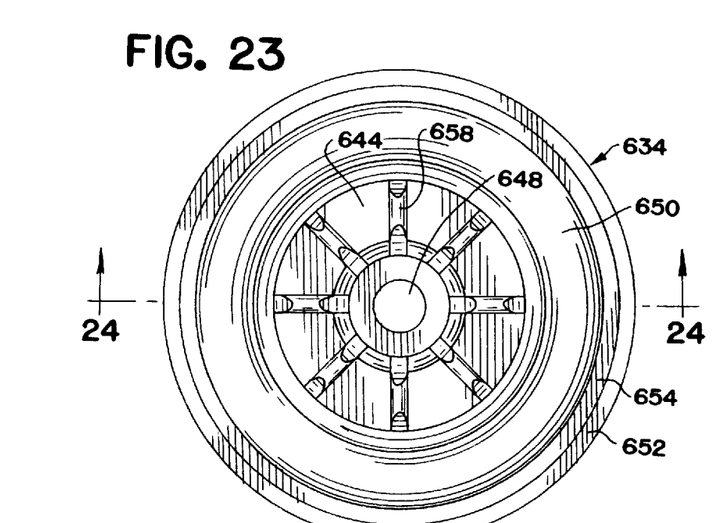
FIG. 23 is a top plan view of another alternative embodiment of a seal member constructed in accordance with the invention.
Figure 24:
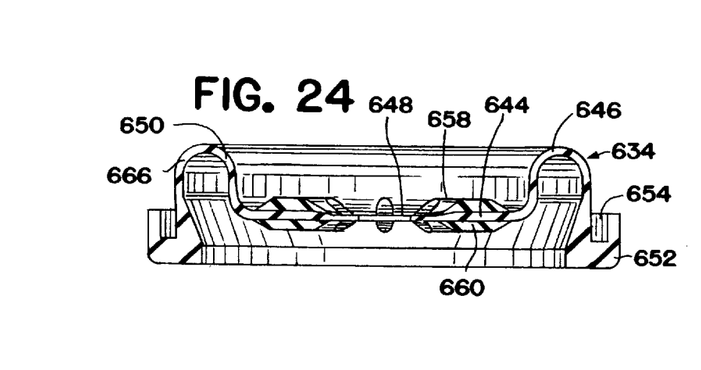
FIG. 24 is a cross-sectional view taken along line 24—24 in FIG. 23.
Figure 25:
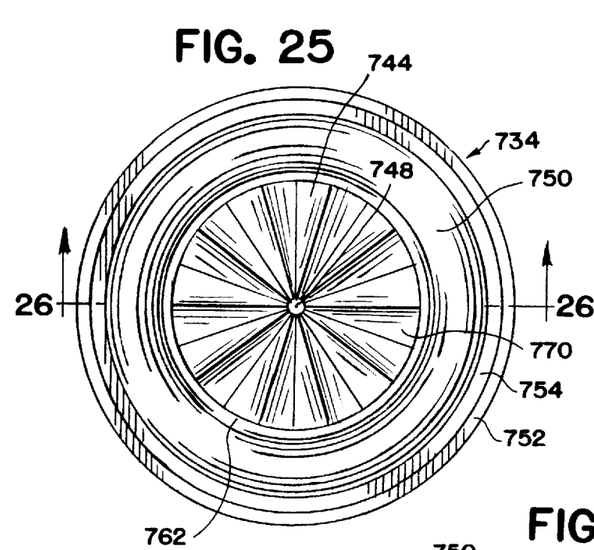
FIG. 25 is a top plan view of another alternative embodiment of a seal member constructed in accordance with the invention.
Figure 26:
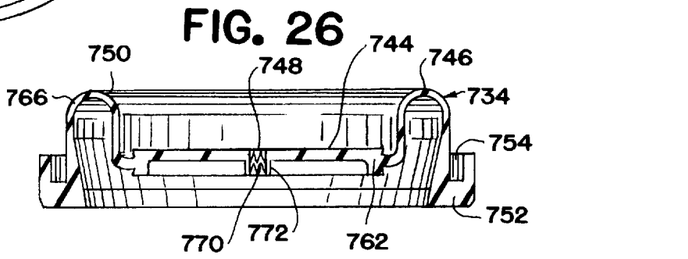
FIG. 26 is a cross-sectional view taken along line 26—26 in FIG. 25.
Figure 27:
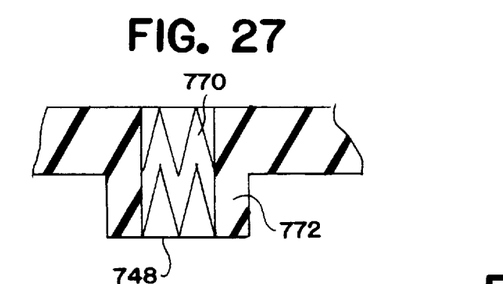
FIG. 27 is an enlarged cross-sectional view of the center portion of the inner section of the seal member as shown in FIG. 26.
Figure 28:
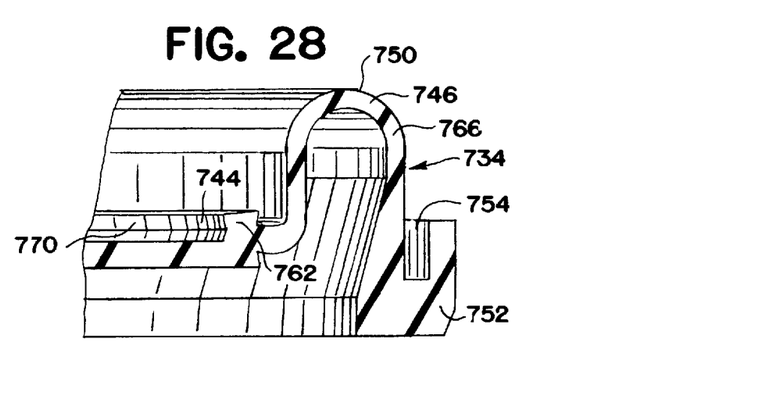
FIG. 28 is an enlarged cross-sectional view of the outer section of the seal member as shown in FIG. 26.

Referring to FIGS. 23–24, there is shown a still further embodiment of a seal member 634 constructed in accordance with the invention. Seal member 634 is similar in construction to seal member 434 except that the corrugated portion includes a single corrugation. The common elements of seal members 434 and 634 are identified by reference numerals having the same last two digits and reference is made to the above discussion of such elements.

Referring to FIGS. 25–28, there is shown yet another embodiment of a seal member 734 constructed in accordance with the invention. Seal member 734 is similar in construction to seal member 634 except that the inner section does not include the proximally or distally facing radial ribs and is provided with radially extending pleats formed therein. The common elements of seal members 634 and 734 are identified by reference numerals having the same last two digits and reference is made to the above discussion of such elements.

Inner section 744 is formed with pleats 770 that extend radially from a center hub portion 772 that surrounds opening 748 and a floating ring portion 762 that separates inner section 744 from outer section 746. In accordance with a preferred embodiment the pleats 770 have an included angle of about 52 degrees. The pleats have a height that is substantially equal to the thickness of the center hub portion 772 and the floating ring portion 762.

The seal members disclosed herein are preferably made from an elastomeric material such as silicon, latex, rubber, polyurethane, Kraton® (a thermoplastic elastomeric A-B-A, styrene-isoprene-styrene, block copolymer manufactured by Shell Chemical Company) or the like.

From the foregoing it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:

1. A trocar assembly for providing communication into an anatomical cavity, comprising:
   (a) a trocar tube defining an interior lumen having an open distal end portion and an open proximal end portion for accommodating axial movement of an elongate instrument of lesser cross-sectional dimension therethrough;
   (b) a housing adjoining said proximal end portion of said trocar tube defining a chamber having open distal and proximal end portions that communicate with said lumen and permit axial movement of an elongate instrument therethrough;
   (c) an elastomeric seal member positioned in said chamber for sealing said proximal end portion of said chamber, said seal member having a distal surface and a proximal surface, said seal member having an inner section and an outer section, said inner section having an opening formed therein for permitting an elongate instrument to pass therethrough in sealing engagement therewith, said seal member having a corrugated portion formed in said outer section in surrounding relationship with said opening so as to maintain the sealing engagement with an elongate instrument during off-centering of an instrument with respect to said seal member; and
   (d) an annular floating ring located immediately adjacent and extending from at least one of said distal and proximal surfaces of said seal member to separate said inner section from said outer section so that off-center movement of an elongate instrument extending through said opening causes lateral movement of said outer section while maintaining said inner section in sealing engagement with the instrument.

2. The trocar assembly as defined in claim 1 herein said ring is a rigid material.

3. The trocar assembly as defined in claim 1 wherein said ring is a semi-rigid material.

4. The trocar assembly as defined in claim 1 wherein said ring is integrally formed as an annular area of said seal member having an increased thickness.

5. The trocar assembly as defined in claim 1 wherein said ring is an annular plastic member molded into said seal member.

6. A trocar assembly for providing communication into an anatomical cavity, comprising:
   (a) a trocar tube defining an interior lumen having an open distal end portion and an open proximal end portion for accommodating axial movement of an elongate instrument of lesser cross-sectional dimension therethrough;
   (b) a housing adjoining said proximal end portion of said trocar tube defining a chamber having open distal end proximal end portions that communicate with said lumen and permit axial movement of an elongate instrument therethrough; and
   (c) an elastomeric seal member positioned in said chamber for sealing said proximal end portion of said chamber, said seal member having a distal end surface and a proximal surface, said seal member having an inner section and an outer section, said inner section having an opening formed therein for permitting an elongate instrument to pass therethrough in sealing engagement therewith, an annular floating ring located immediately adjacent and extending from at least one of said distal and proximal surfaces of said seal member to separate said inner section from said outer section so that off-center movement of an elongate instrument extending through said opening causes lateral movement of said outer section while maintaining said inner section in sealing engagement with the instrument.

7. The trocar assembly as defined in claim 6 wherein said ring is a rigid material.

8. The trocar assembly as defined in claim 6 wherein said ring is a semi-rigid material.

9. The trocar assembly as defined in claim 6 wherein said ring is integrally formed as an annular area of said seal member having an increased thickness.

10. A trocar assembly for providing communication into an anatomical cavity, comprising:
    (a) a trocar tube defining an interior lumen having an open distal end portion and an open proximal end portion for accommodating axial movement of an elongate instrument of lesser cross-sectional dimension therethrough;
    (b) a housing adjoining said proximal end portion of said trocar tube defining a chamber having open distal and proximal end portions that communicate with said lumen and permit axial movement of an elongate instrument therethrough;
    (c) an elastomeric seal member positioned in said chamber for sealing said proximal end portion of said chamber, said seal member having an inner section and an outer section, said inner section having an opening formed therein for permitting an elongate instrument to pass therethrough in sealing engagement therewith, said seal member having a corrugated portion formed in said outer section in surrounding relationship with said opening so as to maintain the sealing engagement with an elongate instrument during off-centering of an instrument with respect to said seal member; and (d) an annular floating ring secured in direct contact with said seal member so that off-center movement of an elongate instrument extending through said opening causes lateral movement of said outer section while maintaining said inner section in sealing engagement with the instrument.

11. The trocar assembly as defined in claim 10 herein said ring is a rigid material.

12. The trocar assembly as defined in claim 10 wherein said ring is a rigid material.

13. A trocar assembly for providing communication into an anatomical cavity, comprising:

(a) a trocar tube defining an interior lumen having an open distal end portion and an open proximal end portion for accommodating axial movement of an elongate instrument of lesser cross-sectional dimension therethrough;

(b) a housing adjoining said proximal end portion of said trocar tube defining a chamber having open distal and proximal end portions that communicate with said lumen and permit axial movement of an elongate instrument therethrough;

(c) an elastomeric seal member positioned in said chamber for sealing said proximal end portion of said chamber, said seal member having an inner section and an outer section, said inner section having an opening formed therein for permitting an elongate instrument to pass therethrough in sealing engagement therewith and (d) an annular floating ring secured in direct contact with said seal member so that off-center movement of an elongate instrument extending through said opening causes lateral movement of said outer section while maintaining said inner section in sealing engagement with the instrument.

* * * * *